United States Patent [19]

Vigh et al.

[11] Patent Number: 5,277,901
[45] Date of Patent: Jan. 11, 1994

[54] OPHTHALMIC COMPOSITIONS AND METHODS FOR PRESERVING AND USING SAME

[75] Inventors: Joseph E. Vigh, Placentia; Priscilla Lo, Carlsbad; Anthony J. Dziabo, Lake Forest; Michelle P. Wong, Tustin, all of Calif.

[73] Assignee: Allergan, Inc., Irvine, Calif.

[21] Appl. No.: 912,862

[22] Filed: Jul. 13, 1992

Related U.S. Application Data

[63] Continuation-in-part of Ser. No. 461,181, Jan. 5, 1990, Pat. No. 5,145,643, and a continuation-in-part of Ser. No. 461,161, Jan. 5, 1970, Pat. No. 5,171,526.

[51] Int. Cl.$^5$ .............. A61K 31/74; A61K 31/425; A61K 31/14
[52] U.S. Cl. .............. 424/78.04; 424/78.07; 514/396; 514/642; 514/912
[58] Field of Search .............. 514/396, 642, 588, 912; 424/78.04, 78.07, 94.4

[56] References Cited

U.S. PATENT DOCUMENTS

| | | | |
|---|---|---|---|
| Re. 32,672 | 5/1988 | Huth et al. | 252/95 |
| 3,771,989 | 11/1973 | Pera et al. | 514/642 |
| 3,874,870 | 4/1975 | Green et al. | 71/67 |
| 3,910,296 | 10/1975 | Karageozian et al. | 134/2 |
| 3,912,451 | 10/1975 | Gaglia, Jr. | 422/30 |
| 4,025,617 | 5/1977 | Green et al. | 424/78 |
| 4,029,817 | 6/1977 | Blanoc et al. | 424/329 |
| 4,168,112 | 9/1979 | Ellis et al. | 351/160 |
| 4,250,269 | 2/1981 | Buckman et al. | 524/236 |
| 4,304,894 | 12/1981 | Andrews et al. | 526/310 |
| 4,443,429 | 3/1984 | Smith et al. | 424/78 |
| 4,499,077 | 2/1985 | Stockel et al. | 424/661 |
| 4,525,346 | 6/1985 | Stark | 514/642 |
| 4,532,128 | 7/1985 | Sheldon et al. | 424/78 |
| 4,568,517 | 2/1986 | Kaspar et al. | 422/30 |
| 4,615,882 | 10/1986 | Stockel | 424/80 |
| 4,654,208 | 3/1987 | Stockel et al. | 514/642 |
| 4,783,488 | 11/1988 | Ogunbiyi et al. | 514/635 |
| 4,786,436 | 11/1988 | Ogunbiyi et al. | 252/352 |
| 4,836,986 | 6/1989 | Ogunbiyi et al. | 422/28 |
| 4,908,209 | 3/1990 | McIntosh, Jr. et al. | 424/409 |
| 4,935,232 | 6/1990 | McIntosh | 424/78 |

FOREIGN PATENT DOCUMENTS 63-13112 4/1988 Japan .
2139260A 11/1984 United Kingdom .

OTHER PUBLICATIONS

The Buckman Toxicity Profile (Jul. 25, 1984.)
The Buckman Technical Specifications (Sep. 23, 1981.)
The Buckman Material Safety Data Sheet (Aug. 13, 1984.)
The Croda, Inc. Bulletin-Crodacel Q (L,M&S) (Jun. 24, 1986.)
The Croda, Inc. Bulletin-Croquat L (Oct. 16, 1982.)
The Croda, Inc. Material Safety Data Sheet (lauroyl quaternized hydroxyethyl cellulose), Jan. 11, 1987.
The Croda, Inc. Material Safety Data Sheet (cocoyl quaternized hydroxyethyl cellulose) Jan. 22, 1987.
The Croda, Inc. Material Safety Data Sheet (stearoyl quaternized hydroxyethyl cellulose) Jan. 11, 1987.
Gennaro, A., Remington's Pharmaceutical Sciences, 17th Edition, pp. 1562-1563, 1985.

Primary Examiner—Zohreh A. Fay
Attorney, Agent, or Firm—Frank J. Uxa

[57] ABSTRACT

Ophthalmic compositions, such as those used to care for contact lenses, methods of preserving such compositions, and methods for disinfecting contact lenses using certain of such compositions are disclosed. The compositions may comprise an ophthalmically acceptable, liquid aqueous medium and, included therein, an effective preserving or disinfecting amount of a combination of certain oxygen-containing ionene polymers and other antimicrobial agents, preferably certain urea components.

22 Claims, No Drawings

OPHTHALMIC COMPOSITIONS AND METHODS FOR PRESERVING AND USING SAME

RELATED APPLICATION

This application is a continuation-in-part of co-pending applications Ser. No. 461,181, filed Jan. 5, 1990 now U.S. Pat. No. 5,145,643, and Ser. No. 461,161, filed Jan. 5, 1990 now U.S. Pat. No. 5,171,526, the disclosure of each of which is hereby incorporated in its entirety by reference herein.

BACKGROUND OF THE INVENTION

This invention relates to ophthalmic compositions and methods for preserving and using such compositions. More particularly, the present invention relates to ophthalmic compositions, e.g., useful in caring for contact lenses, which include one or more of certain ionene polymers as preservatives or disinfectants, and to methods for disinfecting and/or preserving using such compositions.

Various compositions, e.g., solutions, are used in association with contact lenses to ensure that the lenses may be safely, comfortably and conveniently worn. Contact lens care compositions, for example, disinfecting compositions, preserving compositions, cleaning compositions, wetting compositions, conditioning compositions and the like, often utilize at least one disinfectant or preservative, depending on the type of composition, for disinfecting or preserving contact lenses after wear or preserving the lens care composition itself. A contact lens disinfecting composition generally has sufficient antimicrobial activity so that when the composition is contacted with a lens to be disinfected, microorganisms associated with the lens are killed or otherwise removed and the contact lens is effectively disinfected within a reasonable time, e.g., in the range of about 0.1 hour to about 12 hours. A contact lens disinfecting composition may be termed a microbiocidal composition. In contrast, a contact lens preserving composition has sufficient antimicrobial activity, often less of such activity than is present in a contact lens disinfecting composition, so that when the composition is contacted with a contact lens substantially no increase in the microorganism population in the composition is obtained. A contact lens preserving composition may be termed a microbiostatic composition or a microbiocidal composition. Contact lens care compositions are preserved to prevent any substantial increase in the population of contaminating microorganisms in the compositions and, thereby, to extend their shelf life. Such preserved contact lens care compositions may be termed microbiostatic compositions. Some preservatives used in lens preserving compositions or in preserved compositions may also be used as disinfecting agents in lens disinfecting compositions.

Various compounds are known for use as preserving agents in contacts lens preserving compositions and preserved contact lens care compositions. Examples include thimerosal, benzalkonium chloride and chlorhexidine. However, these preserving agents are known to exhibit ocular toxicity which may result in irritation or sensitivity to the eye. The degree of ocular toxicity increases when these agents are utilized as disinfecting agents. Further, a soft contact lens, a rigid gas permeable contact lens (RGP) or a hard contact lens can absorb or adsorb these compounds. This causes the contact lens to retain the irritating compound and contributes to the eye irritation and sensitivity which may result.

Stark U.S. Pat. No. 4,525,346 discloses a contact lens disinfecting solution and preserved contact lens care compositions containing 1-tris (2-hydroxyethyl) ammonium-2-butenyl-4-poly [1-dimethyl ammonium-2-butenyl]-w-tris (2-hydroxyethyl-) ammonium the salt of which has a pharmaceutically acceptable anion. The quaternary ammonium polymer disclosed in this Stark patent is capable of causing irritation and sensitivity to some contact lens wearers.

Japanese Patent Publication 63131124 discloses a liquid composition for contact lens care including as an antimicrobial component a polymeric condensate of a diamine, such as N, N, N', N'- tetramethyl 1,2-diaminoethane, and a dihalogen compound, such as 1,2-dichloroethane. Such polymeric condensates include no oxygen. Further, there is no suggestion that other polymeric condensates are useful as antimicrobial agents in the contact lens care context.

Other conventional methods of contact lens chemical disinfection utilize one or more active disinfecting agents in an aqueous medium, for example a chlorhexidine/thimerosal solution or a relatively mild solution of hydrogen peroxide. Some of these disinfecting solutions, such as those named above, are cytotoxic and are known to be adsorbed or absorbed onto or into a contact lens and cause the lens to elicit a cytotoxic response after disinfection. For example, contact lenses which have been soaked in a disinfecting hydrogen peroxide solution are to be treated to remove residual hydrogen peroxide, e.g., by soaking in a catalase solution, before they may be comfortably and safely worn again. If residual hydrogen peroxide remains on the lenses, then irritation or injury to the eye may result. A lens disinfecting system employing a substantially nonoxidative disinfectant composition is particularly useful since the risk of introducing active oxidizing agents into the eye is substantially eliminated.

Ellis et al U.S. Pat. No. 4,168,112 discloses treating an ionically charged contact lens with a lens solution containing an oppositely charged ionic polymer to form a hydrophilic polyelectrolyte complex on the lens surface. This complex forms a hydrogel and acts as a cushion which provides comfort to the eye. Ionene polymers are among the many ionic polymers disclosed by Ellis et al. In addition, Ellis et al discloses that other additives, such as preservatives, e.g., benzalkonium chloride, ethylenediaminetetraacetic acid, mercurials and chlorobutanol, can be included in the lens treating solutions. Ellis et al does not distinguish between ionene polymers, nor is there any suggestion than any ionene polymers are useful as preservatives or disinfectants in the contact lens care context.

Stockel et al U.S. Pat. No. 4,499,077 discloses oxidative contact lens disinfecting compositions including stabilized chlorine dioxide and a quaternary ammonium compound which is a copolymer of at least one mono- or di-tertiary amine and a dihalo organic compound. Stockel U.S. Pat. No. 4,654,208 discloses oxidative contact lens disinfecting compositions including one or more of the quaternary ammonium copolymers noted above in this paragraph plus a potentiating amount of a oxidizing agent. Neither of the Stockel et al patents disclose nonoxidative contact lens care compositions using such quaternary ammonium copolymers.

Trager et al U.S. Pat. No. 4,539,330 discloses compositions and methods for sterilizing contact lenses and preserving ocular medications which involve using imidazolidinyl urea and imidazolidinyl urea derivatives. Such components, in order to seek to meet the current stringent preservation/disinfection test criteria, need to be present in relatively high concentrations, which may have adverse effects on the lens being treated and/or on the wearer of the treated lens.

In general, it is advantageous to reduce the amount of disinfectant and/or preservative used in the contact lens care context. For example, with reduced amounts of such materials present, adverse reactions to the compositions are reduced. Also, the cost of obtaining effective contact lens disinfection and preserved ophthalmic compositions is reduced.

Thus, it is readily apparent that a continuing need exists for safe and efficacious compositions that can be used as contact lens disinfecting and preserving compositions and as preserved contact lens care compositions.

SUMMARY OF THE INVENTION

New disinfecting and preserving compositions and methods, particularly such compositions and methods directed to contact lens care, have been discovered. The present compositions include effective disinfectants and/or preservatives and are preferably substantially non-oxidative. Thus, for example, a contact lens can be effectively disinfected in a reasonable length of time. Also, contact lens care products can be effectively preserved against growth of contaminating microorganisms. Importantly, such disinfecting and preserving activities are achieved and the contact lenses disinfected, preserved or otherwise cared for using the present compositions can be safely and comfortably worn with little or no risk of eye irritation or sensitivity, e.g., from the presence of residual oxidizing agent.

In one broad aspect of the invention, compositions, preferably substantially non-oxidative compositions, useful for disinfecting a contact lens are provided. Preserved compositions, preferably substantially non-oxidative preserved compositions, are also provided. These compositions include an ophthalmically acceptable, preferably sterile, medium, preferably a liquid aqueous medium. Included within this medium is an effective disinfecting, or preserving, amount of a combination of (1) an ophthalmically acceptable, quaternary ammonium polymer selected from ionene polymers containing an oxygen atom covalently bonded to two carbon atoms and mixtures thereof, and (2) one or more other, e.g., complementary and/or potentiating, antimicrobial agents, preferably an ophthalmically acceptable urea component selected from imidazolidinyl urea, derivatives thereof and mixtures thereof. Methods of disinfecting, or preserving, a contact lens include contacting the lens to be disinfected, or preserved, with an appropriate composition, as described herein.

Such combinations of quaternary ammonium polymers and other antimicrobial agents, preferably urea components, are effective disinfectants and preservatives in the contact lens care context, preferably without the need for oxidizing agents. With the presently useful combinations being employed, effective disinfection and preservation is achieved, preferably with reduced concentrations of quaternary ammonium polymers and other antimicrobial agents being used relative to compositions in which only one of these materials is used as the sole disinfectant or preservative. Contact lenses which are disinfected, or otherwise treated using the present compositions can be safely and comfortably worn with little or no risk of eye irritation or sensitivity.

Preserved compositions, e.g., contact lens care compositions, which include an ophthalmically acceptable medium, preferably containing one or more components effective to beneficially affect a contact lens and/or the wearing of a contact lens, are included within the scope of the present invention. Such preserved compositions include an effective preserving amount of a combination of quaternary ammonium polymers and other antimicrobial agents, preferably urea components, as described herein, and preferably are substantially non-oxidative.

DETAILED DESCRIPTION OF THE INVENTION

The present invention is applicable to disinfecting all types of lenses, e.g., contact lenses, which are benefited by such disinfecting. Such lenses, e.g., conventional soft contact lenses, RGPs and hard contact lenses, may be made of any suitable material or combination of materials and may have any suitable configuration. The invention is also applicable to preserving compositions, such as contact lens care compositions, and other eye care products which are benefited by being preserved.

One important feature of the compositions of the present invention is the inclusion of an effective, e.g., for disinfecting and/or preserving, amount of a combination of (1) at least one ophthalmically acceptable, quaternary ammonium polymer selected from the group consisting of ionene polymers containing an oxygen atom covalently bonded to two carbon atoms, hereinafter referred to as "(C—O—C) ionene polymers", and mixtures thereof, and (2) at least one other antimicrobial agent, preferably an ophthalmically acceptable urea component selected from imidazolidinyl urea, derivatives thereof and mixtures thereof. Without wishing to limit the invention to any particular theory of operation, it is believed that the combinations useful in the present invention are sufficiently active to provide the desired degree of disinfecting or preserving without causing substantial eye irritation or sensitivity.

The presently useful quaternary ammonium polymers are distinguished from the quaternary ammonium polymer described in Stark U.S. Pat. No. 4,525,346 and the polymeric condensate described in Japanese Patent Publication 63131124. In the Stark patent and the Japanese Publication, the quaternary ammonium polymer and the polymeric condensate are not (C—O—C) ionene polymers. The presently useful quaternary ammonium polymers provide the desired antimicrobial activity without causing substantial eye irritation and sensitivity.

The presently useful quaternary ammonium polymers preferably have the following repeating unit

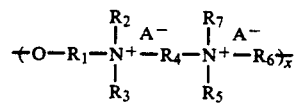

wherein $R_1$, $R_4$ and $R_6$ are each independently selected from alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from ophthalmically acceptable anions, and x is the number of repeating units in the polymer and is an integer in the range of about 5 to about 30. A particularly useful quaternary ammonium polymer has the following repeating unit

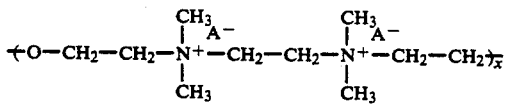

The number of repeating units per polymer molecule, represented by x, is more preferably about 8 to about 30, especially about 14.

Examples of ophthalmically acceptable anions include chloride ($Cl^-$), bromide, iodide, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is $Cl^-$.

In one particularly useful embodiment, the quaternary ammonium polymer has a molecular weight in the range of about 500 to about 5000.

Methods for producing the presently useful quaternary ammonium polymers are described in Buckman et al U.S. Pat. No. 4,250,269, which patent is hereby incorporated in its entirety herein by reference. A specific example of a quaternary ammonium polymer useful in the present invention is poly (oxyethylene (dimethyliminio) ethylene-(dimethyliminio) ethylene dichloride), such as that sold by Buckman Laboratories, Inc. under the trademark WSCP.

The present compositions include one or more other, e.g., complementary and/or potentiating, antimicrobial agents. Examples of such other antimicrobial agents include, but are not limited to, thimerosal, sorbic acid, 1.5-pentanedial, alkyl triethanolamines, boric acid, ophthalmically acceptable salts of any of the above, 3-chloroallyl-3, 5, 7, triaza-1-azonia adamantine chloride, phenylmercuric salts and mixtures thereof. Particularly useful other antimicrobial agents are certain ophthalmically acceptable urea components.

The presently useful urea components are selected from imidazolidinyl urea, imidazolidinyl derivatives and mixtures thereof. Such urea components should be ophthalmically acceptable in the concentrations in which they are employed. Further, such urea components, in combination with the presently useful quaternary ammonium polymers, should have sufficient antimicrobial activity to provide for the desired disinfecting and/or preserving.

Preferred urea components for use in the present invention include imidazolidinyl urea, N-(hydroxymethyl)-N-(1,3-dihydroxymethyl-2 5-dioxy-4-imidazolidinyl)-N'-(hydroxymethyl) urea and mixtures thereof, with the specific above-named imidazolidinyl derivative being more preferred. Commercially available urea components useful in the present invention include those sold by Sutton Laboratories, Inc. under the trademarks Germall II and Germall 115.

The presently useful quaternary ammonium polymers and other antimicrobial agents, preferably urea components, are preferably dispersible or soluble in the ophthalmically acceptable medium. Since contact lens disinfecting, preserving and other care compositions are most often solutions, the quaternary ammonium polymers and other antimicrobial agents are more preferably soluble in the medium. The amount of quaternary ammonium polymers and other antimicrobial agents employed in the present compositions is that sufficient to effect the desired result. Care should be taken to avoid excessive amounts of quaternary ammonium polymers and other antimicrobial agents. Not only are such materials quite expensive, but the use of large excesses may result in some degree of eye irritation and/or sensitivity. The presently useful quaternary ammonium polymer and other antimicrobial agent, preferably urea component, each is preferably present in an amount in the range of about 0.00001% to about 1%, more preferably about 0.0001% to about 0.5%, by weight per volume of ophthalmically acceptable medium.

Ophthalmically acceptable salts may include one or more ophthalmically acceptable anions, e.g., as noted above, or ophthalmically acceptable cations, in particular alkali and alkali metal cations.

Materials which provide more than one beneficial or desired property to the present compositions may also be included. For example, certain combinations of quaternary ammonium compounds which possess both antimicrobial activity and wetting properties may be included. Each of these agents/materials may be included in the present compositions in an amount effective to provide the beneficial or desired property or properties. The compositions of the present invention include an ophthalmically acceptable medium, preferably an ophthalmically acceptable liquid aqueous medium. This medium often acts as a carrier, e.g., as a solvent, for the other components in the composition. A material is "ophthalmically acceptable" if the material can be placed into a mammalian eye without causing any substantial damage or harm to the eye. One particularly useful ophthalmically acceptable medium is water. Preferably, the medium, and in fact the entire composition, is sterile.

One or more additional components can be included in the present compositions based on the particular application for which the compositions are formulated. Thus, the present compositions can be formulated as disinfecting compositions, cleaning compositions, wetting compositions, conditioning compositions, soaking compositions and the like. Also, the present compositions can be formulated to be useful in performing two or more contact lens caring operations. For example, a disinfecting/cleaning composition, or a cleaning/conditioning composition or even an all purpose lens care composition can be formulated and such multi-functional compositions are included within the scope of the present invention.

The additional component or components included in the present compositions are chosen to impart or provide at least one beneficial or desired property to the compositions. Such additional components may be selected from components which are conventionally used in one or more contact lens care compositions. Examples of such additional components include buffering agents, cleaning agents, wetting agents, surfactants, nutrient agents, sequestering agents, viscosity builders, tonicity agents, contact lens conditioning agents, antioxidants, pH adjustors, and the like. These additional components are each included in the present compositions in an amount effective to impart or provide the beneficial or desired property to the compositions. For example, such additional components may be included in the present compositions in amounts similar to the amounts of such components used in other, e.g., conventional, contact lens care products.

Useful buffering agents include, but not limited to, acetate buffers, citrate buffers, phosphate buffers and borate buffers. Acids and bases may be used to adjust the pH of the present compositions as needed. Preferably, the present compositions have ophthalmically acceptably pHs.

Useful wetting agents include, but are not limited to, polyvinyl alcohol, poloxamers, polyvinyl pyrrollidone, hydroxypropyl methyl cellulose and mixtures thereof.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

Useful viscosity builders include, but are not limited to, hydroxyethyl cellulose, hydroxy methyl cellulose, polyvinyl pyrrolidone, hydroxypropylmethyl cellulose, polyvinyl alcohol and mixtures thereof.

Useful antioxidants include, but are not limited to, sodium metabisulfite, sodium thiosulfate, N-acetylcysteine, butylated hydroxyanisole, butylated hydroxytoluene and mixtures thereof.

In a particularly useful embodiment, the quaternary ammonium polymer/urea component-containing compositions further include at least one enzyme effective to remove debris from a contact lens. Among the types of debris that form on a contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et al U.S. Pat. No. RE 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus, II Alkaline Proteases", Biotechnology and Bioengineering, Vol. XII, pp 213-249 (1970) and Keay, L. and Moser, P. W., "Differentiation of Alkaline Proteases form Bacillus Species" Biochemical and Biophysical Research Comm., Vol 34, No. 5, pp 600-604, (1969).

The subtilisin enzymes are broken down into two sub-classes, subtilisin A and subtilisin B. In the subtilisin A grouping are enzymes derived from such species as *B. subtilis, B. licheniformis* and *B. pumilis.* Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *B. polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the excipient it contains.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent. Thus, for any given enzyme, there is a particular pH range in which that enzyme will function best. The determination of such range can readily be done by known techniques.

The present compositions may be used in the care of a contact lens, e.g., to disinfect the lens, to otherwise treat the lens and/or to make wearing the lens safe and comfortable. The present compositions, formulated appropriately, may be used in conventional contact lens care regimens by using the present compositions in place of prior conventional compositions. In many instances, these contact lens care regimens involve contacting the lens with the present composition in an amount, and at conditions, effective to obtain the beneficial or desired contact lens care result. For example, a contact lens to be disinfected may be contacted with a disinfecting composition, e.g., aqueous solution, according to the present invention, preferably at a temperature in the range of about 0° C. to about 100° C., more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time to substantially disinfect the lens being treated. Such contacting times can be in the range of about 1 minute to about 12 hours or more.

After this contacting, the disinfected contact lens can be taken from the composition and placed directly in an eye, e.g., a human eye, for safe and comfortable wear. Alternately, after being disinfected, the contact lens can be contacted with a second medium, e.g., a liquid aqueous medium such as a preserved isotonic saline solution, prior to being placed in the eye of the wearer of the disinfected contact lens.

The contact lens care compositions disclosed herein are adaptable for use in most types of contact lens care equipment, such as ultrasonic cleaners and the like.

The following examples are set out to illustrate, but not limit, the scope of this invention.

EXAMPLES 1 TO 4

A series of four (4) compositions were prepared by blending the constituents together. These compositions were as follows:

| CONSTITUENT | COMPOSITION[3][4] | | | |
|---|---|---|---|---|
| | 1 | 2 | 3 | 4 |
| Ionene polymer[1] concentrate, wt. % | 0.005 | 0.01 | | 0.005 |
| Urea Component, wt % | 0.05 | 0.005 | 0.005 | |
| Disodium ethylene diamine etraacetate, wt. % | 0.05 | 0.05 | 0.05 | 0.05 |
| Purified water, USP | QS | QS | QS | QS |

[1] A concentrate containing 60% by weight of poly (oxyethylene (dimethyliminio)-ethylene (dimethyliminio) ethylene dichloride) sold under the trademark WSCP by Buckman Laboratories, Inc.
[2] N-(hydroxymethyl)-N-(1,3-dihydroxymethyl-2,5-dioxo-4-imidazolidinyl)-N'-(hydroxymethyl) urea sold under the trademark Germall II by Sutton Laboratories, Inc.
[3] Hydrochloric acid and sodium hydroxide were added to give a pH within the range of 7.6 to 7.8.
[4] Each of the compositions was ionically and osmotically balanced by the addition of salts, such as sodium chloride, and buffers, such as borate buffers.

Each of these compositions was tested for preservative efficacy and passed the USP preservative efficacy criteria. However, when each of the compositions was tested for preservative efficacy in accordance with the more stringent BP-88 test procedure, Composition 1 passed while the other three compositions failed.

These results demonstrate that combinations of certain quaternary ammonium polymers, as described herein, at concentrations ranging from 30 ppm to 60 ppm by weight and certain urea components, as described herein, at concentrations ranging from 50 ppm to 500 ppm by weight are effective antimicrobial preservatives for contact lens care products. Composition 1 is quite effective as a contact lens disinfecting solution in a standard contact lens care regimen, with or without simultaneous or sequential enzymatic lens cleaning as part of the regimen.

EXAMPLE 5

Composition 1, described above, is used to disinfect a conventional soft contact lens as follows. 7.5 ml of the composition is provided at room temperature. The contact lens to be disinfected is placed in the composition. Four hours after the contact lens is first introduced into the composition, it is removed from the composition and placed directly into the wearer's eye. It is found that after four hours, the contact lens is effectively disinfected. Also, the lens wearer experiences no discomfort or eye irritation form wearing the disinfected contact lens. Alternately, after the contacting for four hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 6

Example 5 is repeated except that about 50 ppm by weight of subtilisin A, based on the total weight of the Composition 1 used, is added at the same time the contact lens to be disinfected is added to the composition. Four hours after the contact lens is first introduced into the composition, it is removed from the composition, rinsed with Composition 1, or with preserved or non-preserved sterile isotonic saline solution, and placed directly into the wearer's eye. It is found that after four hours, the contact lens is effectively disinfected and cleaned of protein-based debris. Also, the lens wearer experiences no discomfort or eye irritation from wearing the disinfected and cleaned contact lens.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
   contacting a contact lens with a composition including a liquid medium and an effective disinfecting amount of a combination of (1) a quaternary ammonium polymer which is ophthalmically acceptable and is selected from the group consisting of ionene polymers containing an oxygen atom covalently bonded to two carbon atoms and mixtures thereof, and (2) at least one other antimicrobial agent at conditions to effectively disinfect said contact lens.

2. The method of claim 1 wherein said composition includes a liquid aqueous medium.

3. The method of claim 1 wherein said at least one other antimicrobial agent is an urea component which is ophthalmically acceptable and is selected from the group consisting of imidazolidinyl urea, derivatives thereof and mixtures thereof.

4. The method of claim 1 which further comprises contacting said contact lens in a liquid medium with at least one enzyme capable of removing debris from a contact lens in an amount effective to remove debris from said contact lens.

5. The method of claim 1 wherein said quaternary ammonium polymer has a repeating unit

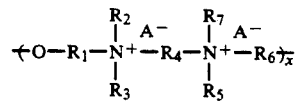

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 5 to about 30.

6. The method of claim 3 wherein said quaternary ammonium polymer is poly (oxyethylene (dimethyliminio) ethylene dimethyliminio) ethylene dichloride and said urea component is selected from the group consisting of imidazolidinyl urea, N-(hydroxymethyl)-N-(1,3-dihydroxymethyl-2,5-dioxy-4-imidazolidinyl)-N'-(hydroxymethyl) urea and mixtures thereof.

7. A method for preserving an ophthalmically acceptable medium comprising:
   contacting an ophthalmically acceptable medium with an effective preserving amount of a combination of (1) a quaternary ammonium polymer which is ophthalmically acceptable and is selected for the group consisting of ionene polymers containing an oxygen atom covalently bonded to two carbon atoms and mixtures thereof, and (2) at least one other antimicrobial agent which is ophthalmically acceptable at conditions to effectively preserve said ophthalmically acceptable medium.

8. The method of claim 7 wherein said ophthalmically acceptable medium is a liquid aqueous medium.

9. The method of claim 7 wherein said at least one other antimicrobial agent is an urea component which is ophthalmically acceptable and is selected from the group consisting of imidazolidinyl urea, derivatives thereof and mixtures thereof.

10. The method of claim 7 wherein said quaternary ammonium polymer has a repeating unit

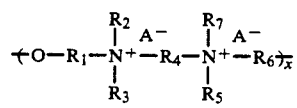

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 5 to about 30.

11. The method of claim 9 wherein said quaternary ammonium polymer is poly (oxyethylene (dimethyliminio) ethylene dimethyliminio) ethylene dichloride and said urea component is selected from the group consisting of imidazolidinyl urea, N-(hydroxymethyl)-N-(1,3-dihydroxymethyl-2,5-dioxy-4-imidazolidinyl)-N'-(hydroxymethyl) urea and mixtures thereof.

12. A composition useful for disinfecting a contact lens comprising an ophthalmically acceptable, liquid aqueous medium and, included therein, an effective disinfecting amount of a combination of (1) a quaternary ammonium polymer which is ophthalmically acceptable and is selected from the group consisting of ionene polymers containing an oxygen atom covalently bonded to two carbon atoms and mixtures thereof, and (2) an urea component which is ophthalmically acceptable and is selected from the group consisting of imidazolidinyl urea, derivatives thereof and mixtures thereof.

13. The composition of claim 12 wherein each of said quaternary ammonium polymer and said urea component is present in an amount in the range of about 0.00001% to about 1% by weight per volume of said ophthalmically acceptable liquid aqueous medium.

14. The composition of claim 12 which further comprises at least one enzyme capable of removing debris from a contact lens in an amount effective to remove debris from a debris laden contact lens.

15. The composition of claim 12 wherein said quaternary ammonium polymer has a repeating unit

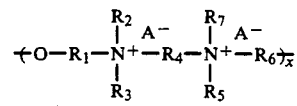

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 5 to about 30.

16. The composition of claim 12 wherein said quaternary ammonium polymer is poly (oxyethylene (dimethyliminio) ethylene dimethyliminio) ethylene dichloride and said urea component is selected from the group consisting of imidazolidinyl urea, N-(hydroxymethyl)-N-(1,3-dihydroxymethyl-2,5-dioxy-4-imidazolidinyl)-N'-(hydroxymethyl) urea and mixtures thereof.

17. The composition of claim 16 wherein said urea component is N-(hydroxymethyl)-N-(1,3-dihydroxymethyl-2,5-dioxy-4-imidazolidinyl)-N'-(hydroxymethyl)urea.

18. A preserved composition comprising an ophthalmically acceptable medium and, included therein, an effective preserving amount of a combination of (1) a quaternary ammonium polymer which is ophthalmically acceptable and is selected from the group consisting of ionene polymers containing an oxygen atom covalently bonded to two carbon atoms and mixtures thereof, and (2) an urea component which is ophthalmically acceptable and is selected from the group consisting of imidazolidinyl urea, derivatives thereof and mixtures thereof.

19. The composition of claim 18 wherein said ophthalmically acceptable medium is a liquid aqueous medium.

20. The composition of claim 18 wherein said polymer quaternary ammonium polymer has a repeating unit

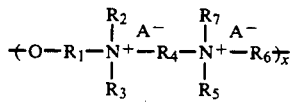

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 8 to about 30.

21. The composition of claim 18 wherein said quaternary ammonium polymer is poly (oxyethylene (dimethyliminio) ethylene dimethyliminio) ethylene dichloride and said urea component is selected from the group consisting of imidazolidinyl urea, N-(hydroxymethyl)-N-(1,3-dihydroxymethyl-2,5-dioxy-4-imidazolidinyl)-N'-(hydroxymethyl) urea and mixtures thereof.

22. The method of claim 21 wherein said urea component is N-(hydroxymethyl)-N-(1,3-dihydroxymethyl-2,5-dioxy-4-imidazolidinyl)-N'-(hydroxymethyl) urea.

* * * * *